(12) United States Patent  
Choi et al.

(10) Patent No.: US 11,075,344 B2  
(45) Date of Patent: Jul. 27, 2021

(54) ORGANIC DEVICE AND IMAGE SENSOR

(71) Applicants: Samsung Electronics Co., Ltd., Suwon-si (KR); Seoul National University, R&DB Foundation, Seoul (KR)

(72) Inventors: Yeong Suk Choi, Suwon-si (KR); Soo Young Park, Seoul (KR); Sung Young Yun, Suwon-si (KR); Min-Woo Choi, Seoul (KR); Ji Eon Kwon, Seoul (KR); Hyeong-Ju Kim, Seoul (KR)

(73) Assignees: Samsung Electronics Co., Ltd., Gyeonggi-do (KR); Seoul National University R&DB Foundation, Seoul (KR)

( * ) Notice: Subject to any disclaimer, the term of this patent is extended or adjusted under 35 U.S.C. 154(b) by 22 days.

(21) Appl. No.: 16/526,230

(22) Filed: Jul. 30, 2019

(65) Prior Publication Data

US 2020/0152888 A1    May 14, 2020

(30) Foreign Application Priority Data

Nov. 13, 2018 (KR) .................. 10-2018-0138943

(51) Int. Cl.
 *H01L 51/00* (2006.01)
 *H01L 51/44* (2006.01)
 (Continued)

(52) U.S. Cl.
 CPC ........ *H01L 51/0072* (2013.01); *C07D 471/04* (2013.01); *H01L 27/307* (2013.01);
 (Continued)

(58) Field of Classification Search
 CPC ............................... B82Y 10/00; C08G 61/12
 (Continued)

(56) References Cited

U.S. PATENT DOCUMENTS 6,303,943 B1 * 10/2001 Yu .................. B82Y 10/00  
                                                         257/40  
8,436,127 B2    5/2013 Mishra et al.  
(Continued)

FOREIGN PATENT DOCUMENTS

JP    2012031157 A    2/2012  
KR    101486694 B1    1/2015  
(Continued)

OTHER PUBLICATIONS

Lim, Seon-Jeong et al_Organic-on-silicon 2014.  
(Continued)

*Primary Examiner* — Khanh T Nguyen  
(74) *Attorney, Agent, or Firm* — Harness, Dickey & Pierce, P.L.C.

(57) ABSTRACT

Disclosed are an organic device including a first electrode and a second electrode facing each other and an active layer between the first electrode and the second electrode, wherein the active layer includes compound represented by Chemical Formula 1, and an image sensor including the same.

[Chemical Formula 1]

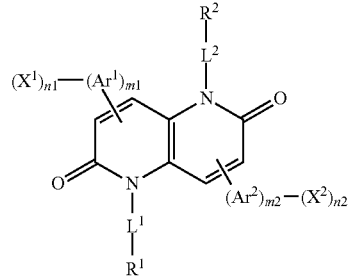

In Chemical Formula 1, $L^1$, $L^2$, $R^1$, $R^2$, $Ar^1$, $Ar^2$, $X^1$, $X^2$, m1, m2, n1, and n2 are the same as described in the detailed description.

15 Claims, 7 Drawing Sheets

(51) Int. Cl.
*C07D 471/04* (2006.01)
*H01L 27/30* (2006.01)

(52) U.S. Cl.
CPC ...... *H01L 51/0068* (2013.01); *H01L 51/0069* (2013.01); *H01L 51/44* (2013.01)

(58) Field of Classification Search
USPC .......................................................... 257/40
See application file for complete search history.

(56) References Cited

U.S. PATENT DOCUMENTS

| | | |
|---|---|---|
| 8,525,577 B2 | 9/2013 | Yofu et al. |
| 2015/0144846 A1 | 5/2015 | Nanson et al. |
| 2018/0040826 A1 | 2/2018 | Kobilka et al. |

FOREIGN PATENT DOCUMENTS

| | | | |
|---|---|---|---|
| KR | 20150023515 A | 3/2015 | |
| WO | WO 2013/182262 A1 * | 12/2013 | ............. H01L 51/46 |
| WO | WO-2015178115 A1 | 11/2015 | |

OTHER PUBLICATIONS

Ihama, Mikio et al_CMOS Image Sensor_2009.
Aihara, Satoshi et al_Stacked Image Sensor_IEEE_Trans, vol. 56, Nov. 2009.
Jap.J.Appl.Phys_2007.

* cited by examiner

ORGANIC DEVICE AND IMAGE SENSOR

CROSS-REFERENCE TO RELATED APPLICATION

This application claims priority to and the benefit of Korean Patent Application No. 10-2018-0138943, filed in the Korean Intellectual Property Office on Nov. 13, 2018, the entire contents of which are incorporated herein by reference.

BACKGROUND

1. Field

An organic device and an image sensor are disclosed.

2. Description of the Related Art

A photoelectric device converts light into an electrical signal using photoelectric effects. It may include a photodiode, a phototransistor, and the like, and it may be applied to an image sensor, a solar cell, an organic light emitting diode, and the like.

An image sensor including a photodiode requires high resolution and thus a small pixel. At present, a silicon photodiode is widely used, but it has a problem of deteriorated sensitivity since it has a small absorption area due to small pixels. Accordingly, an organic material that is capable of replacing silicon has been researched.

An organic material has a high extinction coefficient and selectively absorbs light in a particular wavelength region depending on a molecular structure, and thus may simultaneously replace a photodiode and a color filter and resultantly improve sensitivity and contribute to high integration.

SUMMARY

An embodiment provides an organic device capable of selectively absorbing light in a narrow wavelength region and improving heat resistance and processability.

Another embodiment provides an image sensor including the organic device.

According to an embodiment, an organic device includes a first electrode and a second electrode facing each other and an active layer between the first electrode and the second electrode, wherein the active layer includes a compound represented by Chemical Formula 1.

[Chemical Formula 1]

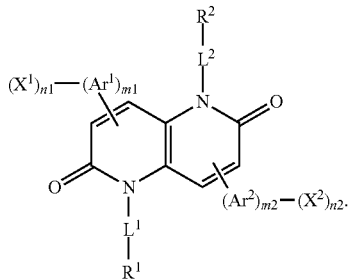

In Chemical Formula 1,
$L^1$ and $L^2$ are independently a single bond, a substituted or unsubstituted C1 to C20 alkylene group, a substituted or unsubstituted C6 to C30 arylene group, a substituted or unsubstituted divalent C3 to C30 heterocyclic group, a fused ring thereof, or a combination thereof, $R^1$ and $R^2$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C20 alkoxy group, a substituted or unsubstituted C2 to C20 ester group, a halogen, a cyano group, or a combination thereof, $Ar^1$ and $Ar^2$ are independently a substituted or unsubstituted C6 to C30 arylene group, a substituted or unsubstituted divalent C3 to C30 heterocyclic group, a fused ring thereof, or a combination thereof, $X^1$ and $X^2$ are independently a hydrocarbon cyclic group substituted with an electron withdrawing group, a heterocyclic group substituted with an electron withdrawing group, a substituted or unsubstituted nitrogen-containing cyclic group, a fused ring thereof, or a combination thereof, m1 and m2 are independently an integer ranging from 0 to 3, and n1 and n2 are independently an integer ranging from 0 to 3, provided that n1 and n2 are not simultaneously 0.

In some embodiments, $Ar^1$ and $Ar^2$ of Chemical Formula 1 may independently be a substituted or unsubstituted phenylene group, a substituted or unsubstituted naphthylene group, a substituted or unsubstituted anthracenylene group, a substituted or unsubstituted fluorenylene group, a substituted or unsubstituted thiophenylene group, a substituted or unsubstituted furanylene group, a substituted or unsubstituted selenophenylene group, a substituted or unsubstituted tellurophenylene group, a substituted or unsubstituted silolylene group, a substituted or unsubstituted pyrrolylene group, a substituted or unsubstituted imidazolylene group, a substituted or unsubstituted pyridinylene group, a substituted or unsubstituted pyrimidinylene group, a substituted or unsubstituted triazinylene group, a fused ring thereof, or a combination thereof.

In some embodiments, the electron withdrawing group may include a halogen atom, a C1 to C20 haloalkyl group, a cyano group, a dicyanovinyl group, or a combination thereof.

In some embodiments, $X^1$ and $X^2$ of Chemical Formula 1 may independently be one of groups listed in Group 1.

[Group 1]

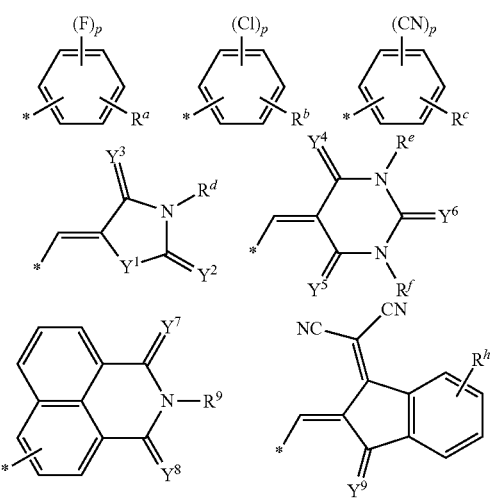

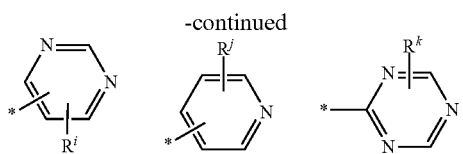

In Group 1, $Y^1$ to $Y^9$ are independently O, S, or Se, $R^a$ to $R^k$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof, p is an integer ranging from 1 to 5, and

* is a linking point.

In some embodiments, the compound may be represented by Chemical Formula 1a.

[Chemical Formula 1a]

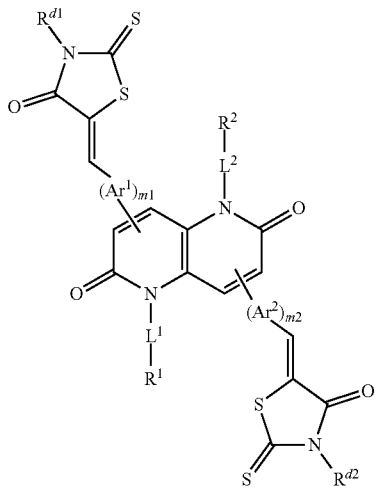

In Chemical Formula 1a, $L^1$ and $L^2$ are independently a single bond, a substituted or unsubstituted C1 to C20 alkylene group, a substituted or unsubstituted C6 to C30 arylene group, a substituted or unsubstituted divalent C3 to C30 heterocyclic group, a fused ring thereof, or a combination thereof, $R^1$ and $R^2$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C20 alkoxy group, a substituted or unsubstituted C2 to C20 ester group, a halogen, a cyano group, or a combination thereof, $Ar^1$ and $Ar^2$ are independently a substituted or unsubstituted C6 to C30 arylene group, a substituted or unsubstituted divalent C3 to C30 heterocyclic group, a fused ring thereof, or a combination thereof, $R^{d1}$ and $R^{d2}$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof, and m1 and m2 are independently an integer ranging from 0 to 3.

In some embodiments, $Ar^1$ and $Ar^2$ of Chemical Formula 1a may independently be a substituted or unsubstituted phenylene group, a substituted or unsubstituted naphthylene group, a substituted or unsubstituted anthracenylene group, a substituted or unsubstituted fluorenylene group, a substituted or unsubstituted thiophenylene group, a substituted or unsubstituted furanylene group, a substituted or unsubstituted selenophenylene group, a substituted or unsubstituted tellurophenylene group, a substituted or unsubstituted silolylene group, a substituted or unsubstituted pyrrolylene group, a substituted or unsubstituted imidazolylene group, a substituted or unsubstituted pyridinylene group, a substituted or unsubstituted pyrimidinylene group, a substituted or unsubstituted triazinylene group, a fused ring thereof, or a combination thereof.

In some embodiments, a HOMO energy level of the compound may be about 5.2 eV to about 5.8 eV.

In some embodiments, the compound may be configured to selectively absorb light in a red wavelength region, a green wavelength region, or a blue wavelength region.

In some embodiments, the compound may be an n-type semiconductor and the active layer may further include a p-type semiconductor capable of providing a pn junction with the compound.

In some embodiments, a HOMO energy level of the p-type semiconductor may be about 5.2 eV to about 5.8 eV.

In some embodiments, the compound may be configured to selectively absorb light in a red wavelength region, a green wavelength region, or a blue wavelength region, and the p-type semiconductor may be configured to selectively absorb light in a same wavelength region as an absorption wavelength region of the compound.

In some embodiments, a peak absorption wavelength of the compound and a peak absorption wavelength of the p-type semiconductor may commonly belong to one region of about 410 nm to about 480 nm, about 510 nm to about 560 nm, and about 620 nm to about 690 nm.

In some embodiments, the active layer may further include fullerene or a fullerene derivative.

According to another embodiment, an electronic device includes the organic device.

According to another embodiment, an image sensor includes the organic device.

In some embodiments, the image sensor may include a semiconductor substrate on one surface of the organic device. The semiconductor substrate may include a plurality of photodiodes.

In some embodiments, the organic device may be configured to selectively absorb first visible light in a red wavelength region, a green wavelength region, or a blue wavelength region. The photodiode may include a first photodiode and a second photodiode. The first photodiode may be configured to sense second visible light in a red wavelength region, a green wavelength region, or a blue wavelength region. The second photodiode may be configured to sense third visible light in a red wavelength region, a green wavelength region, or a blue wavelength region. The first visible light, the second visible light, and the third visible light may be different from each other.

In some embodiments, the image sensor may further include a color filter layer on or under the organic device.

In some embodiments, the color filter layer may further include a first color filter and a second color filter. The first color filter may overlap with the first photodiode and may be configured to selectively transmit light including the second visible light. The second color filter may overlap with the second photodiode and may be configured to selectively transmit light including the third visible light.

According to another embodiment, an electronic device includes the image sensor.

The organic device may selectively absorb light in a narrow wavelength region to increase wavelength selectivity and may improve electrical characteristics.

DETAILED DESCRIPTION

Figure 1:
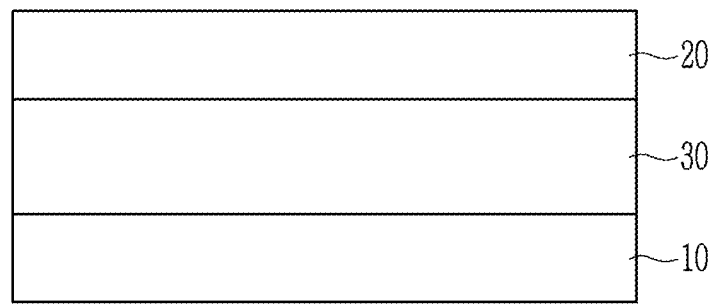
FIG. 1 is a cross-sectional view of an organic device according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, "combination" may refer to a mixture of two or more and a stack structure of two or more.

As used herein, when a definition is not otherwise provided, "substituted" may refer to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" may refer to inclusion of one to three heteroatoms selected from O, S, P, and Si.

As used herein, when a definition is not otherwise provided, "hydrocarbon cyclic group" may refer to a ring group consisting of carbon, including both aromatic and non-aromatic groups, and includes monocyclic, polycyclic, or fused ring polycyclic groups.

As used herein, when a definition is not otherwise provided, "heterocyclic group" is a generic concept of a heteroaryl group, may include an aromatic and non-aromatic ring including at least one heteroatom, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

Hereinafter, a HOMO energy level is expressed as an absolute value from a vacuum level. In addition, when the HOMO energy level is referred to be deep, high, or large, the HOMO energy level has a large absolute value from "0 eV" of the vacuum level, while when the HOMO energy level is referred to be shallow, low, or small, the HOMO energy level has a small absolute value from "0 eV" of the vacuum level.

Hereinafter, a LUMO energy level is expressed as an absolute value from a vacuum level. In addition, when the LUMO energy level is referred to be deep, high, or large, the HOMO energy level has a large absolute value from "0 eV" of the vacuum level, while when the LUMO energy level is referred to be shallow, low, or small, the HOMO energy level has a small absolute value from "0 eV" of the vacuum level.

Hereinafter, an organic device according to an embodiment is described.

The organic device may be in the form of a diode or a transistor. For example, an example of an organic device in the form of a diode will be described.

FIG. 1 is a cross-sectional view of an organic device according to an embodiment.

Referring to FIG. 1, an organic device 100 according to an embodiment includes a first electrode 10 and a second electrode 20 facing each other, and an active layer 30 between the first electrode 10 and the second electrode 20.

A substrate (not shown) may be disposed on a surface of the first electrode 10 or a surface of the second electrode 20. The substrate may be for example made of an inorganic material such as glass, an organic material such as polycarbonate, polymethylmethacrylate, polyethyleneterephthalate, polyethylenenaphthalate, polyamide, polyethersulfone, or a combination thereof, or a silicon wafer.

One of the first electrode 10 and the second electrode 20 is an anode and the other is a cathode. For example, the first electrode 10 may be an anode and the second electrode 20 may be a cathode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AlTO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The active layer 30 may be for example a photoelectric conversion layer, and may convert light of at least one part of a wavelength region of a visible wavelength region into an electric signal, and may for example convert one of light in a blue wavelength region (hereinafter, referred to as "blue light"), light in a green wavelength region (hereinafter, referred to as "green light"), and light in a red wavelength region (hereinafter, referred to as "red light") into an electric signal.

For example, the active layer 30 may convert one of blue light, green light, and red light into an electric signal.

For example, the active layer 30 may selectively absorb light in at least one part of a wavelength region of a visible wavelength region and for example selectively absorb one of blue light, green light, and red light.

For example, the active layer 30 may selectively absorb one of blue light, green light, and red light. Herein, selective absorption of one from the blue light, the green light, and the red light means that a peak absorption wavelength of a light-absorption spectrum exists in one range among the ranges of about 410 nm to about 480 nm, about 510 nm to about 560 nm, and about 620 nm to about 670 nm and a light-absorption spectrum in a corresponding wavelength region is remarkably higher than a light-absorption spectrum in other wavelength regions.

The active layer 30 includes a semiconductor capable of absorbing light in a desired (and/or alternatively predetermined) wavelength region and converting the light into an electric signal. The semiconductor may be an organic semiconductor, an inorganic semiconductor, and/or an organic/inorganic semiconductor.

For example, the active layer 30 may include a compound represented by Chemical Formula 1.

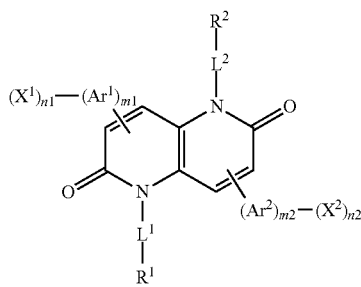

[Chemical Formula 1]

In Chemical Formula 1, $L^1$ and $L^2$ are independently a single bond, a substituted or unsubstituted C1 to C20 alkylene group, a substituted or unsubstituted C6 to C30 arylene group, a substituted or unsubstituted divalent C3 to C30 heterocyclic group, a fused ring thereof, or a combination thereof, $R^1$ and $R^2$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C20 alkoxy group, a substituted or unsubstituted C2 to C20 ester group, a halogen, a cyano group, or a combination thereof, $Ar^1$ and $Ar^2$ are independently a substituted or unsubstituted C6 to C30 arylene group, a substituted or unsubstituted divalent C3 to C30 heterocyclic group, a fused ring thereof, or a combination thereof, $X^1$ and $X^2$ are independently a hydrocarbon cyclic group substituted with an electron withdrawing group, a heterocyclic group substituted with an electron withdrawing group, a substituted or unsubstituted nitrogen-containing cyclic group, a fused ring thereof, or a combination thereof m1 and m2 are independently an integer ranging from 0 to 3, n1 and n2 are independently an integer ranging from 0 to 3, and provided that n1 and n2 are not simultaneously 0.

Since the compound has a structure in which a substituent having electron characteristics is introduced into a naphthyridine-dione core, the compound may simultaneously satisfy light-absorption characteristics and electrical characteristics for selectively absorbing light in a desired (and/or alternatively predetermined) wavelength region of a visible region and may be effectively applied to the active layer 30 that is a photoelectric conversion layer.

The compound may selectively absorb light in one wavelength region of a red wavelength region, a green wavelength region, and a blue wavelength region according to an substituent, and a peak absorption wavelength of the compound may for example belong to one of about 410 nm to about 480 nm, about 510 nm to about 560 nm, and about 620 nm to about 690 nm and may have for example a full width at half maximum (FWHM) of about 50 nm to about 150 nm. Herein, the half width is a width of a wavelength corresponding to half of the height at a maximum absorption point, and when the FWHM is small, it means that light having a narrow wavelength region may be absorbed to exhibit high wavelength selectivity. The full width at half maximum (FWHM) may be for example about 50 nm to about 140 nm, about 50 nm to about 130 nm, about 50 nm to about 120 nm, about 50 nm to about 110 nm, or about 50 nm to about 100 nm.

The compound may have a different energy band gap depending on a substituent, and may have an energy band gap of, for example, about 2.0 eV to about 3.0 eV, about 3.0 eV to about 3.3 eV, or about 1.5 eV to about 2.0 eV.

The HOMO energy level of the compound may be about 5.2 eV to about 5.8 eV, for example about 5.3 eV to about 5.8 eV.

The compound may be a monomer, for example a monomer that may be deposited such as a monomer that may be thermally deposited.

For example, $L^1$ and $L^2$ of Chemical Formula 1 may independently be a single bond or a substituted or unsubstituted C6 to C30 arylene group, for example a single bond, a substituted or unsubstituted phenylene group, a substituted or unsubstituted biphenylene group, or a substituted or unsubstituted naphthylene group.

For example, $R^1$ and $R^2$ of Chemical Formula 1 may independently be hydrogen, a substituted or unsubstituted C1 to C30 alkyl group, a substituted or unsubstituted C6 to C30 aryl group, or a substituted or unsubstituted C1 to C20 alkoxy group.

For example, $Ar^1$ and $Ar^2$ of Chemical Formula 1 may independently be a substituted or unsubstituted phenylene group, a substituted or unsubstituted naphthylene group, a substituted or unsubstituted anthracenylene group, a substituted or unsubstituted fluorenylene group, a substituted or unsubstituted thiophenylene group, a substituted or unsubstituted furanylene group, a substituted or unsubstituted selenophenylene group, a substituted or unsubstituted tellurophenylene group, a substituted or unsubstituted silolylene group, a substituted or unsubstituted pyrrolylene group, a substituted or unsubstituted imidazolylene group, a substituted or unsubstituted pyridinylene group, a substituted or unsubstituted pyrimidinylene group, a substituted or unsubstituted triazinylene group, a fused ring thereof, or a combination thereof.

For example, in Chemical Formula 1, the electron withdrawing group may be a halogen atom, a C1 to C20 haloalkyl group, a cyano group, a dicyanovinyl group, or a combination thereof.

For example, $X^1$ and $X^2$ of Chemical Formula 1 may independently be a halogen-substituted C6 to C30 aryl group, a halogen-substituted C6 to C30 cycloalkyl group, a halogen-substituted C3 to C30 heterocyclic group, a halogen-substituted C6 to C30 fused ring, a haloalkyl group-substituted C6 to C30 aryl group, a haloalkyl group-substituted C6 to C30 cycloalkyl group, a haloalkyl group-substituted C3 to C30 heterocyclic group, a haloalkyl group-substituted C6 to C30 fused ring, a cyano group-substituted C6 to C30 aryl group, a cyano group-substituted C6 to C30 cycloalkyl group, a cyano group-substituted C3 to C30 heterocyclic group, a cyano group-substituted C6 to C30 fused ring, a cyanovinyl group-substituted C6 to C30 cycloalkyl group, a cyanovinyl group-substituted C3 to C30 heterocyclic group, a cyanovinyl group-substituted C6 to C30 fused ring, a dicyanovinyl group-substituted C6 to C30 cycloalkyl group, a dicyanovinyl group-substituted C3 to C30 heterocyclic group, a dicyanovinyl group-substituted C6 to C30 fused ring, or a combination thereof, but are not limited thereto.

For example, $X^1$ and $X^2$ of Chemical Formula 1 may independently be one of groups of Group 1 but are not limited thereto.

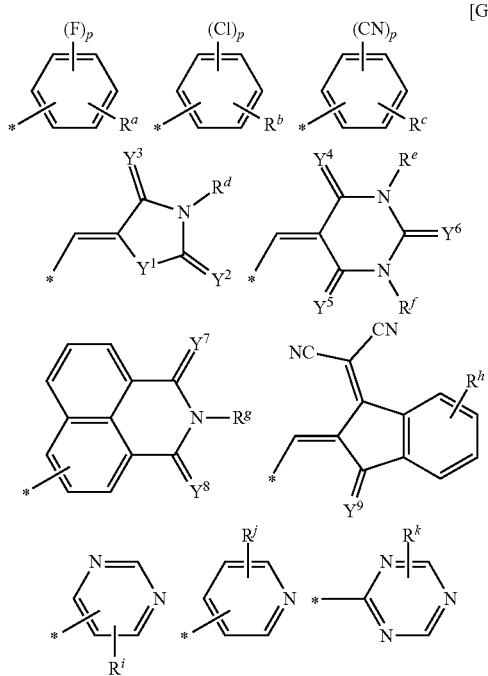

[Group 1]

In Group 1,
$Y^1$ to $Y^9$ are independently O, S, or Se,
$R^a$ to $R^k$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof, p is an integer ranging from 1 to 5, and
* is a linking point.

The compound may be for example represented by Chemical Formula 1a.

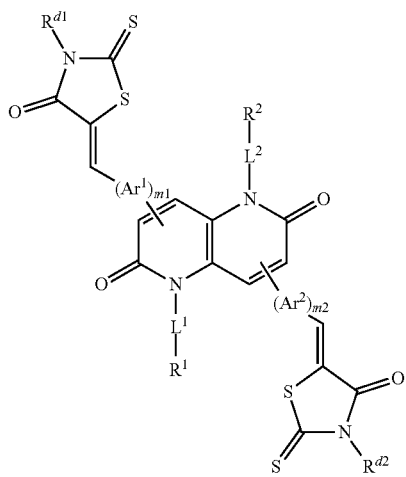

[Chemical Formula 1a]

In Chemical Formula 1a,
$L^1$, $L^2$, $R^1$, $R^2$, $Ar^1$, $Ar^2$, m1, and m2 may be the same as defined in Chemical Formula 1,
$R^{d1}$ and $R^{d2}$ may independently be hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof.

The compound may be included as an n-type semiconductor of the active layer 30.

The active layer 30 may further include one or more n-type semiconductors in addition to the compound and may further include for example fullerene or a fullerene derivative.

The active layer 30 may further include an n-type semiconductor and a p-type semiconductor capable of forming a pn junction.

The p-type semiconductor may be a light absorbing material and can be, for example, an organic light absorbing material. For example, the p-type semiconductor may be a wavelength-selective light-absorbing material that selectively absorbs light in a desired (and/or alternatively predetermined) wavelength region, for example, the p-type semiconductor may be a wavelength-selective organic light-absorbing material.

The p-type semiconductor may be selected in consideration of the optical and electrical matching with the above-mentioned compound.

For example, the p-type semiconductor may selectively absorb light in one wavelength region of a blue wavelength region, a green wavelength region, and a red wavelength region, and may have light-absorption characteristics in a wavelength region common to the above-described compound. For example, the compound and the p-type semiconductor may be capable of absorbing light in a blue wavelength region commonly and may have a peak absorption wavelength in the wavelength region of about 410 nm to about 480 nm commonly. For example, the compound and the p-type semiconductor may be capable of absorbing light in a green wavelength region commonly and may have a peak absorption wavelength in the wavelength region of about 510 nm to about 560 nm commonly. For example, the compound and the p-type semiconductor may be capable of absorbing light in a red wavelength region commonly and may have a peak absorption wavelength in the wavelength region of about 620 nm to about 690 nm commonly.

For example, the p-type semiconductor may be a monomer, for example a monomer that may be deposited.

For example, the p-type semiconductor may be thiophene or a thiophene derivative.

For example, the p-type semiconductor may be a monomer represented by Chemical Formula 2.

EDG-HA-EAG     [Chemical Formula 2]

In Chemical Formula 1,

HA may be a C2 to C30 heterocyclic group including at least one of S, Se, Te, and Si, EDG may be an electron donating group, and EAG may be an electron accepting group.

The active layer 30 may be an intrinsic layer (I layer) in which the p-type semiconductor and the n-type semiconductor are mixed in a bulk heterojunction. Herein, the p-type semiconductor and the n-type semiconductor may be mixed in a volume ratio of about 1:9 to about 9:1, within the range, for example, in a volume ratio of about 2:8 to about 8:2, about 3:7 to about 7:3, about 4:6 to about 6:4, or about 5:5. For example, the p-type semiconductor may be included in the same volume ratio as or in a greater volume ratio than the n-type semiconductor and for example the p-type semiconductor and the n-type semiconductor may be for example mixed in a volume ratio of about 1:1 to about 3:1, for example about 1:1 to about 2:1.

The active layer 30 may be a bilayer including a p-type layer including the p-type semiconductor and an n-type layer including the n-type semiconductor. Herein, each thickness of the p-type layer and the n-type layer may be about 1:9 to about 9:1, for example about 2:8 to about 8:2, about 3:7 to about 7:3, about 4:6 to about 6:4, or about 5:5.

The organic device 100 may further include an anti-reflection layer (not shown) on one surface of the first electrode 10 or the second electrode 20. The anti-reflection layer is disposed at a light incidence side and lowers reflectance of light of incident light and thereby light absorbance is further improved.

For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5 and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as a zinc sulfide; or an organic material such as an amine derivative but is not limited thereto.

In the organic device 100, when light enters from the first electrode 10 or the second electrode 20 and the active layer 30 absorbs light in a desired (and/or alternatively predetermined) wavelength region, excitons may be produced therein. The excitons are separated into holes and electrons in the active layer 30, and the separated holes are transported to an anode that is one of the first electrode 10 and the second electrode 20 and the separated electrons are transported to the cathode that is the other of the first electrode 10 and the second electrode 20 so as to flow a current.

Hereinafter, an organic device according to another embodiment is described.

Figure 2:
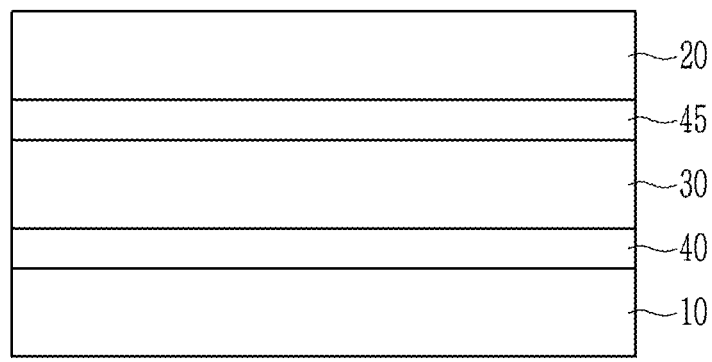
FIG. 2 is a cross-sectional view of an organic device according to another embodiment.

FIG. 2 is a cross-sectional view of an organic device according to another embodiment.

Referring to FIG. 2, an organic device 200 according to the present embodiment includes a first electrode 10 and a second electrode 20 facing each other and an active layer 30 disposed between the first electrode 10 and the second electrode 20, like the organic device 100 in FIG. 1. The first electrode 10, the second electrode 20, and the active layer 30 are the same as described above.

However, the organic device 200 according to the present embodiment further includes charge auxiliary layers 40 and 45 between the first electrode 10 and the active layer 30 and the second electrode 20 and the active layer 30, unlike the above embodiment. The charge auxiliary layers 40 and 45 may make holes and electrons separated in the active layer 30 be transported easily to improve efficiency.

The charge auxiliary layers 40 and 45 may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Each thickness of the charge auxiliary layers 40 and 45 may be for example about 1 nm to about 20 nm.

Either one of the charge auxiliary layers 40 and 45 may be omitted.

The organic device may be various electronic devices such as image sensors, photodetectors, photosensors, solar cells, and organic light emitting diode (OLED), and the like, but is not limited thereto.

The organic device may be for example applied to an image sensor.

Hereinafter, an example of an image sensor including the organic device is described referring to drawings. As an example of an organic image sensor, an organic CMOS image sensor is described.

Figure 3:
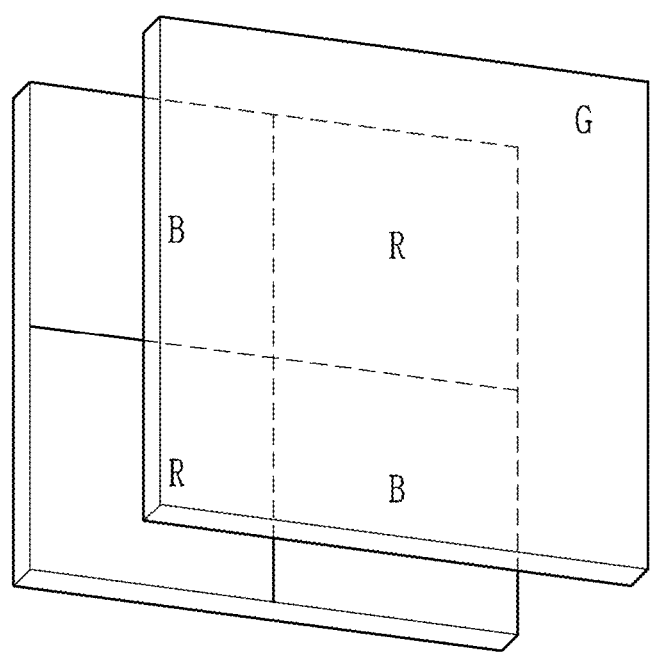
FIG. 3 is a schematic top plan view of an organic CMOS image sensor according to an embodiment.
Figure 4:
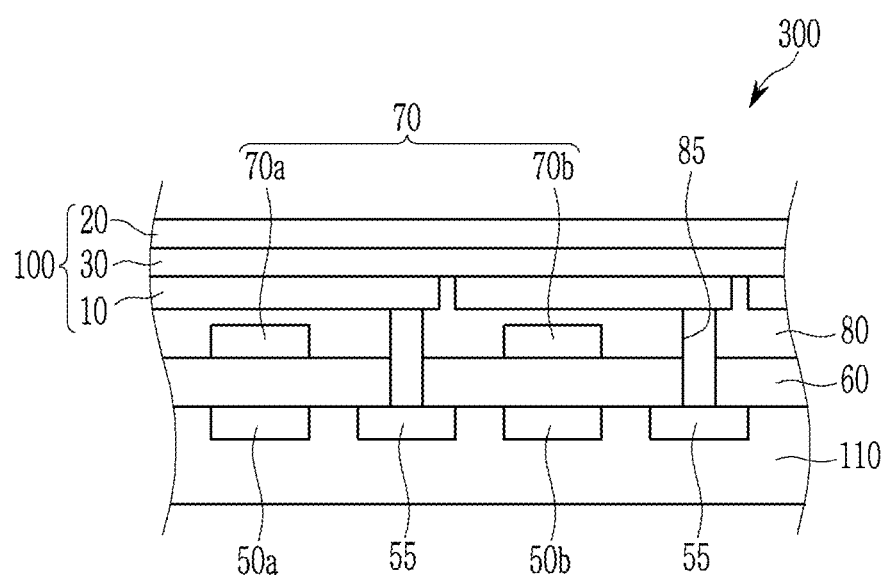
FIG. 4 is a cross-sectional view showing one example of the organic CMOS image sensor of FIG. 3.

FIG. 3 is a schematic top plan view of an organic CMOS image sensor according to an embodiment and FIG. 4 is a cross-sectional view showing one example of the organic CMOS image sensor of FIG. 3.

Referring to FIGS. 3 and 4, an organic CMOS image sensor 300 according to an example embodiment includes a semiconductor substrate 110 integrated with photo-sensing devices 50a and 50b, a transmission transistor (not shown) and a charge storage 55, a lower insulation layer 60, a color filter layer 70, an upper insulation layer 80, and an organic device 100.

The semiconductor substrate 110 may be a silicon substrate and is integrated with the photo-sensing devices 50a and 50b, the transmission transistor (not shown), and the charge storage 55. The photo-sensing devices 50a and 50b may be photodiodes.

The photo-sensing devices 50a and 50b, the transmission transistor, and/or the charge storage 55 may be integrated in each pixel, and as shown in the drawing, the photo-sensing devices 50a and 50b may be respectively included in a blue pixel and a red pixel and the charge storage 55 may be included in a green pixel.

The photo-sensing devices 50a and 50b sense light, the information sensed by the photo-sensing devices may be transferred by the transmission transistor, the charge storage 55 is electrically connected to the organic device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing device 50a and 50b.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70a formed in a blue pixel and a red filter 70b formed in a red pixel. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The organic device 100 is formed on the upper insulation layer 80. The organic device 100 includes a first electrode 10, an active layer 30, and a second electrode 20 as described above. In the drawing, the first electrode 10, the active layer 30, and the second electrode 20 are sequentially stacked, but this disclosure is not limited thereto, and for example they may be stacked in an order of the second electrode 20, the active layer 30, and the first electrode 10.

The first electrode 10 and the second electrode 20 may be all transparent electrodes and the active layer 30 is the same as described above. The active layer 30 may for example selectively absorb light in a green wavelength region and may replace a color filter of a green pixel.

Light in a green wavelength region of light that enters from the second electrode 20 is mainly absorbed by the active layer 30 and photoelectrically converted and light in a remaining wavelength region is transmitted through the first electrode 10 and is sensed by the photo-sensing devices 50a and 50b.

Focusing lens (not shown) may be further formed on the organic device 100. The focusing lens may control a direction of incident light and gather the light in one region. The focusing lens may have a shape of, for example, a cylinder or a hemisphere, but is not limited thereto.

As described above, the organic device 100 has a stack structure thereby a size of an image sensor may be reduced to realize a down-sized image sensor.

For better understanding and ease of description, a structure in which a blue photodiode and a red photodiode are integrated in a semiconductor substrate and a green organic device is disposed thereon is described. However, the present disclosure is not limited to this, and a structure in which a green photodiode and a red photodiode may be integrated in a semiconductor substrate and a blue organic device is disposed thereon or a structure in which a green photodiodes and a blue photodiodes are integrated in the semiconductor substrate, and a red organic device is disposed thereon may be equally applied.

FIG. 4 shows a structure where the organic device of FIG. 1 is stacked, but a structure where the organic device of FIG. 2 is stacked may be equally applied thereto.

The organic device and the organic image sensor may be applied to various electronic devices, for example mobile phones, digital cameras, and the like, but is not limited thereto.

In the above description, an example in which the organic device is implemented in the form of a diode is described. However, the present disclosure is not limited thereto, and an example in which the device is implemented in the form of a transistor such as an organic field-effect transistor may be equally described.

Figure 5:
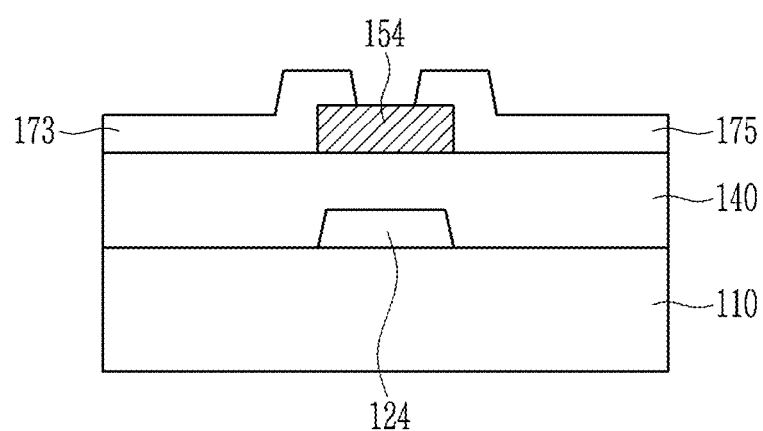
FIG. 5 is a cross-sectional view of an organic device according to another embodiment.

FIG. 5 is a cross-sectional view of an organic device according to another embodiment.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof. However, the present disclosure is not limited thereto, and when the substrate 110 is a silicon substrate, the gate electrode 124 may be formed in the silicon.

A gate insulating layer 140 is formed on the gate electrode 124. The gate insulating layer 140 may be made of an organic material and/or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride ($SiN_x$) and a silicon oxide ($SiO_2$).

An active layer 154 is formed on the gate insulating layer 140. The active layer 154 may include the compound. The active layer 154 may be formed in a solution process such as spin coating, slit coating, or inkjet printing by preparing the compound in a form of a solution. The active layer 154 may be formed by vacuum-depositing or thermal evaporating the compound.

A source electrode 173 and a drain electrode 175 are formed on the active layer 154. The source electrode 173 and the drain electrode 175 may face each other on the active layer 154. The source electrode 173 is electrically connected to the data line (not shown) transferring the data signal. The source electrode 173 and the drain electrode 175 may include at least one metal of gold (Au), copper (Cu), nickel (Ni), aluminum (Al), molybdenum (Mo), chromium (Cr), tantalum (Ta), titanium (Ti), an alloy thereof, or a combination thereof.

Herein, a structure in which the active layer 154 is formed under the source electrode 173 and the drain electrode 175 is described as an example of the organic field-effect transistor. However, the present disclosure is not limited thereto and a structure in which the source electrode 173 and the drain electrode 175 may be formed under the active layer 154 may be equally applied in the same manner.

Herein, the organic field-effect transistor of a bottom gate structure is described as an example of the organic field-effect transistor. However, the present disclosure is not limited thereto and may be equally applied to an organic field-effect transistor of any structure such as an organic field-effect transistor of the top gate structure.

The organic field-effect transistor may be applied to various electronic devices as a switching device and/or a driving device, and the electronic device may include a liquid crystal display (LCD), an organic light emitting diode (OLED) display, an electrophoretic display, an organic photoelectric device, and an organic sensor, but is not limited thereto.

Hereinafter, the embodiments are described in more detail with reference to non-limiting examples. It is to be understood, however, that the following examples are for descriptive purposes only and are not intended to limit the scope of inventive concepts.

SYNTHESIS EXAMPLES

Synthesis Example 1

[Reaction Scheme 1]

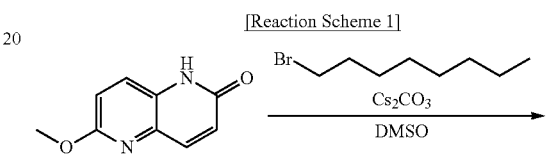

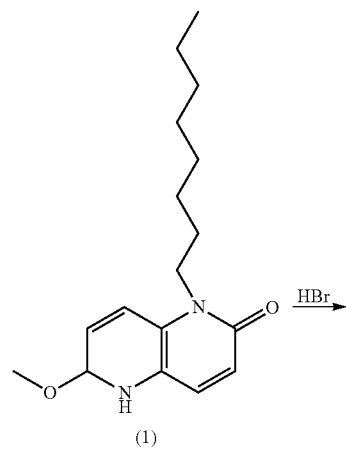

(1)

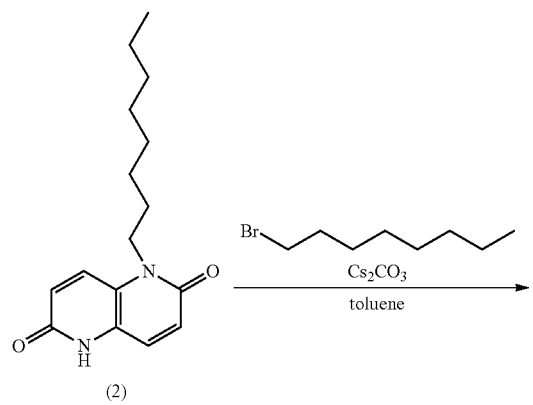

(2)

-continued
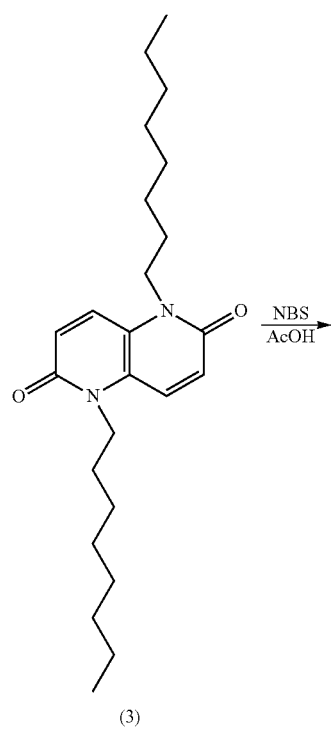
(3)
[Reaction Scheme 2]
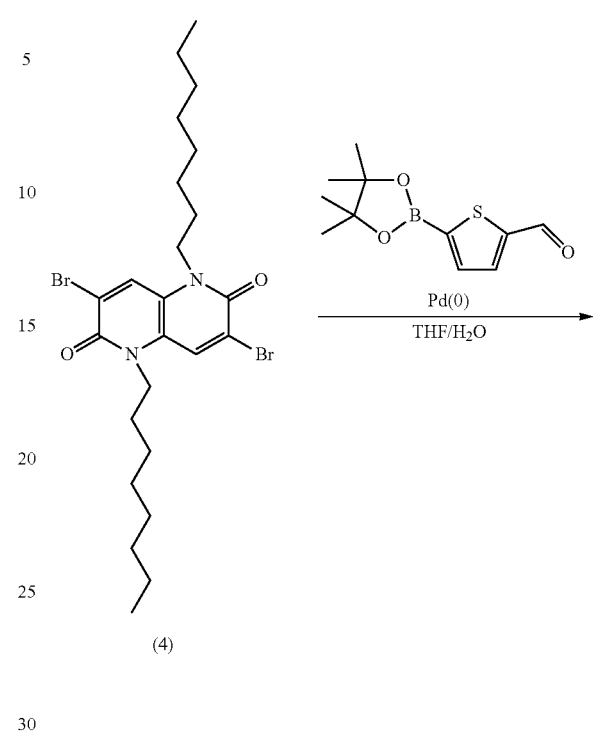
(4)
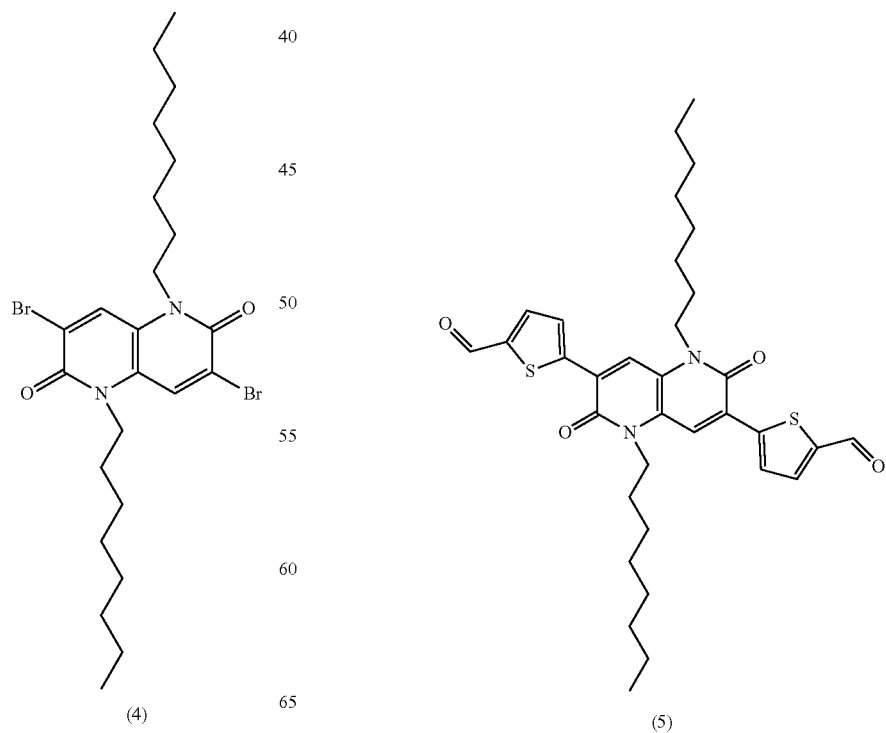
(4)                                   (5)

[Reaction Scheme 3]

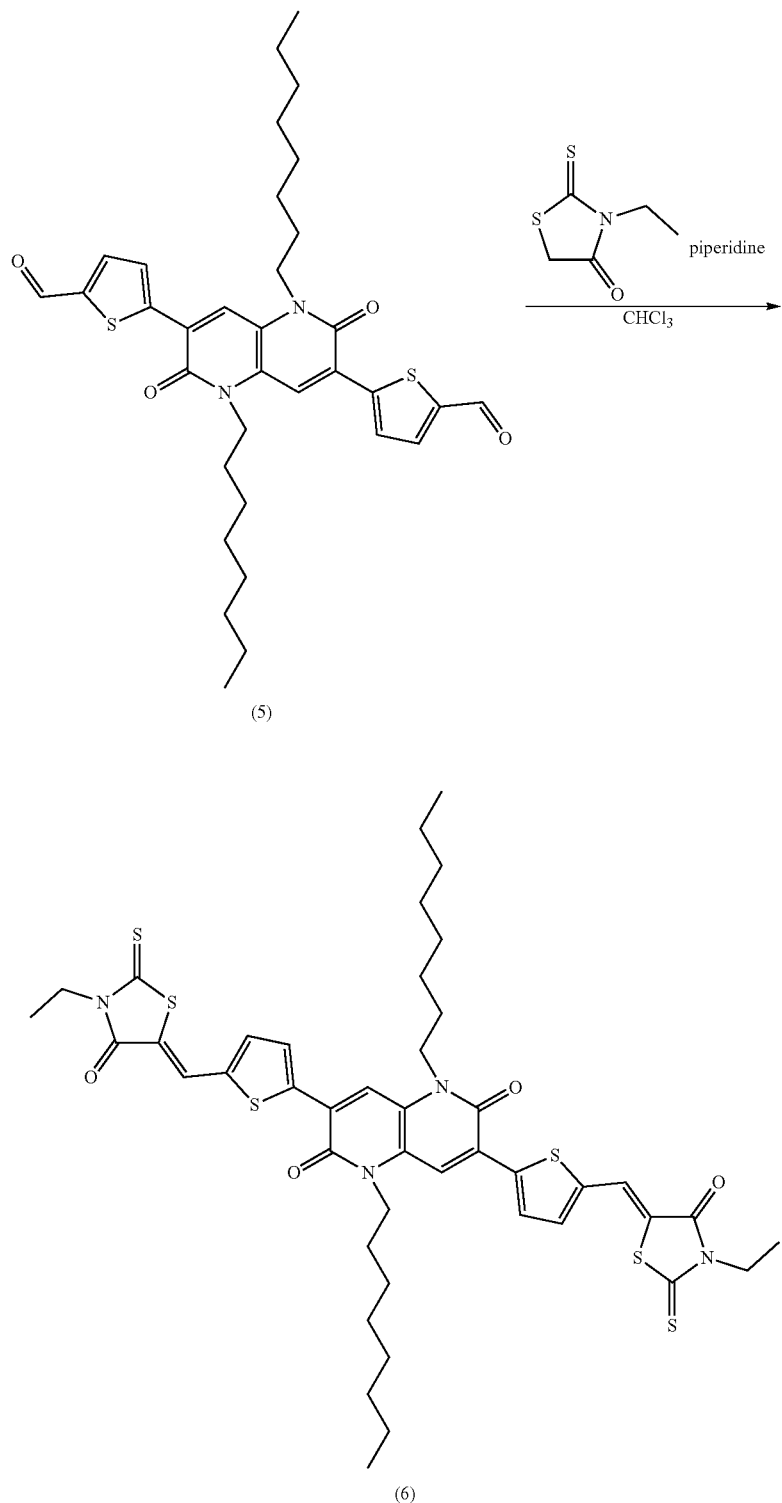

Synthesis of Intermediate 1

6-methoxy-1,5-naphthyridin-2(1H)-one (16 g, 90.8 mmol), cesium carbonate ($Cs_2CO_3$; 32.6 g, 100 mmol), and 1-bromooctane (23.5 mL, 136 mmol) are dissolved in dimethylsulfoxide (DMSO; 160 mL) and then, stirred at 60° C. and allowed to stand for 24 hours. Subsequently, the temperature is decreased down to room temperature, and an organic material is extracted by using ethyl acetate (EA) and water, and the solvent is removed therefrom under vacuum.

Then, 11.1 g of Intermediate (1) as a yellow solid is obtained therefrom through silica gel column. Herein, a yield is 43%.

Synthesis of Intermediate (2)

Intermediate (1) (11.1 g, 38.5 mmol) is dissolved in 48% hydrobromic acid (HBr in water; 80 mL) and then, stirred at 80° C. and allowed to stand for 2 hours. Subsequently, after decreasing the temperature down to room temperature and adjusting pH into 7, a precipitate produced therein is filtered, while washed with n-hexane, and then, vacuum-dried to obtain 9.52 g of Intermediate (2) as a yellow solid. Herein, a yield is 90%.

Synthesis of Intermediate (3)

Intermediate (2) (4.5 g, 16.4 mmol), cesium carbonate (5.88 g, 18.0 mmol), and 1-bromooctane (42.5 mL, 246 mmol) are dissolved in toluene (500 mL) and then, stirred at 130° C. and allowed to stand for 24 hours. Subsequently, the temperature is decreased down to room temperature, and then, an organic material is extracted by using ethyl acetate (EA) and water, and the solvent is removed therefrom under vacuum. Then, 2.06 g of Intermediate (3) as a yellow solid is obtained through silica gel column. Herein, a yield is 33%.

Synthesis of Intermediate (4)

Intermediate (3) (1 g, 2.59 mmol) and N-bromosuccinimide (NBS; 1.29 g, 7.24 mmol) are dissolved in 50 mL of acetic acid and then, stirred at 90° C. and allowed to stand for 24 hours. Subsequently, after decreasing the temperature down to room temperature and removing the solvent therefrom under vacuum, 0.97 g of Intermediate (4) as a yellow powder is obtained through silica gel column. Herein, a yield is 69%.

Synthesis of Intermediate (5)

Intermediate (4) (0.1 g, 0.18 mmol), 5-formyl-2-thiopheneboronic acid pinacol ester (0.13 g, 0.55 mmol), Pd(PPh$_3$)$_4$ (0.021 g, 0.018 mmol), and 3 mL of a K$_2$CO$_3$ aqueous solution at a concentration of 1 M are added to 12 mL of THF and then, stirred at 75° C. and allowed to stand for 24 hours. Subsequently, after decreasing the temperature down to room temperature, an organic material is extracted with CHCl$_3$ and water, and the solvent is removed therefrom under vacuum. Then, 0.034 g of Intermediate (5) is obtained as a red solid through silica gel column. Herein, a yield is 31%.

Synthesis of Final Compound (6)

Intermediate (5) (0.067 g, 0.11 mmol) and 3-ethylrhodanine (0.053 g, 0.33 mmol) are added to 10 mL of CHCl$_3$, 3 drops of piperidine are added thereto, and the obtained mixture stirred at 65° C. and allowed to stand for 24 hours. Subsequently, after decreasing the temperature down to room temperature, an organic material is extracted with CHCl$_3$ and water, and the solvent is removed therefrom under vacuum. Then, 0.056 g of Compound (6) is obtained as a blue solid through silica gel column. Herein, a yield is 57%.

$^1$H NMR (300 MHz, CDCl$_3$, δ): 8.00 (s, 2H), 7.88 (s, 2H), 7.76 (d, 2H), 7.45 (d, 2H), 4.46 (t, 4H), 4.20 (q, 4H), 1.86 (m, 4H), 1.63-1.23 m, 26, 0.90 t, 6.

Synthesis Example 2

[Reaction Scheme 4]

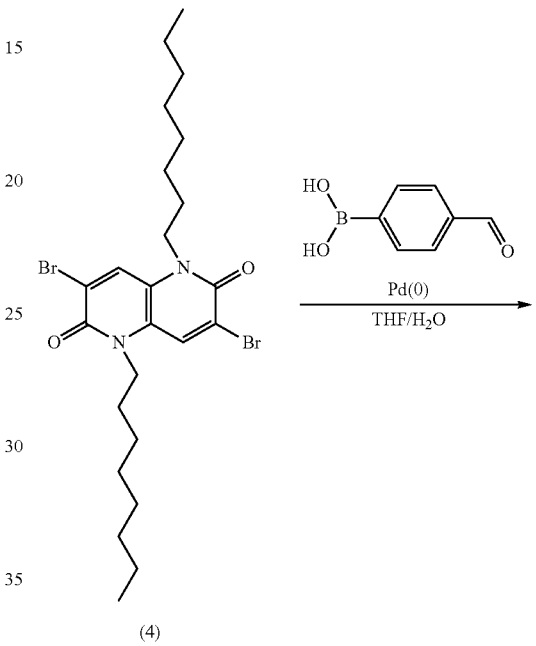

(4)

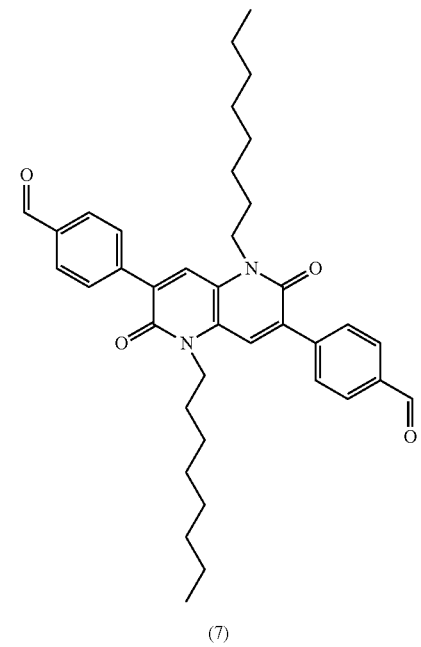

(7)

[Reaction Scheme 5]

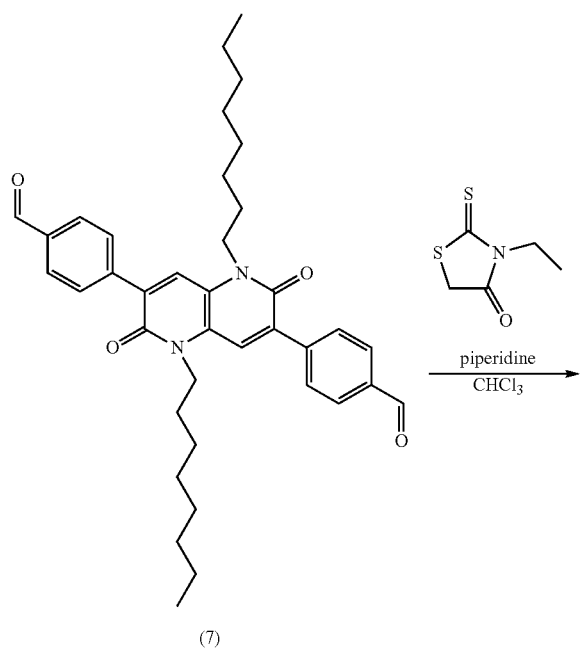

(7)

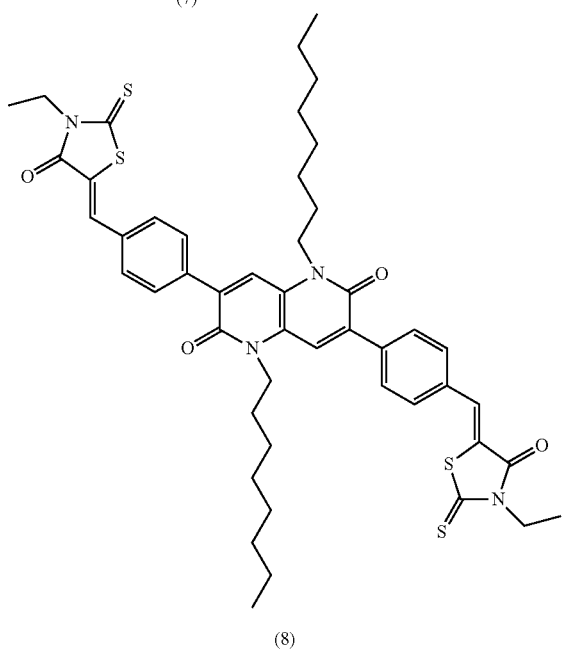

(8)

Synthesis of Intermediate (7)

Intermediate (4) (0.1 g, 0.18 mmol), 4-formylphenylboronic acid (0.083 g, 0.55 mmol), Pd(PPh$_3$)$_4$ (0.021 g, 0.018 mmol), and 2 mL of a K$_2$CO$_3$ aqueous solution at a concentration of 1 M are added to 8 mL of THF and then, stirred at 75° C. and allowed to stand for 24 hours. Subsequently, after decreasing the temperature down to room temperature, an organic material is extracted with CHCl$_3$ and water, and the solvent is removed therefrom under vacuum. Then, 0.077 g of Intermediate (7) is obtained as a cherry red solid through silica gel column. Herein, a yield is 71%.

Synthesis of Final Compound (8)

Intermediate (7) (0.05 g, 0.084 mmol) and 3-ethylrhodanine (0.041 g, 0.25 mmol) are added to 10 mL of CHCl$_3$, 3 drops of piperidine are added thereto, and the obtained mixture is stirred at 65° C. and allowed to stand for 24 hours. Subsequently, after decreasing the temperature down to room temperature, an organic material is extracted with CHCl$_3$ and water, and the solvent is removed therefrom under vacuum. Then, 0.025 g of final Compound (8) is obtained as a blue solid through silica gel column. Herein, a yield is 34%.

$^1$H NMR (300 MHz, CDCl$_3$, δ): 7.91 (s, 4H), 7.77 (s, 2H), 7.72 (d, 2H), 7.62 (d, 4H), 4.37 (t, 4H), 4.22 (q, 4H), 1.82 (m, 4H), 1.56-1.22 m, 26, 0.87 t, 6.

PREPARATION EXAMPLES

Preparation Example 1

Compound (6) of Synthesis Example 1 is deposited on a glass substrate to form a 100 nm-thick thin film under a condition of 10$^{-6}$ torr.

Preparation Example 2

A thin film is formed according to the same method as Preparation Example 1 except for using Compound (8) according to Synthesis Example 2 instead of Compound (6) of Synthesis Example 1.

Evaluation I: Energy Level

An energy level of each thin film according to Preparation Examples 1 and 2 is evaluated by using AC3 (RIKEN KEIKI Co., Ltd.).

The results are shown in Table 1.

TABLE 1

|  | HOMO (eV) | LUMO (eV) | Energy bandgap (eV) |
| --- | --- | --- | --- |
| Preparation Example 1 | 5.58 | 3.82 | 1.76 |
| Preparation Example 2 | 5.77 | 3.66 | 2.11 |

Evaluation II: Light-Absorption Characteristics

Light-absorption characteristics of the thin films according to Preparation Examples 1 and 2 are evaluated.

The light-absorption characteristics are evaluated by using QE 400 VIR (TNE Tech Co., Ltd.).

Figure 6:
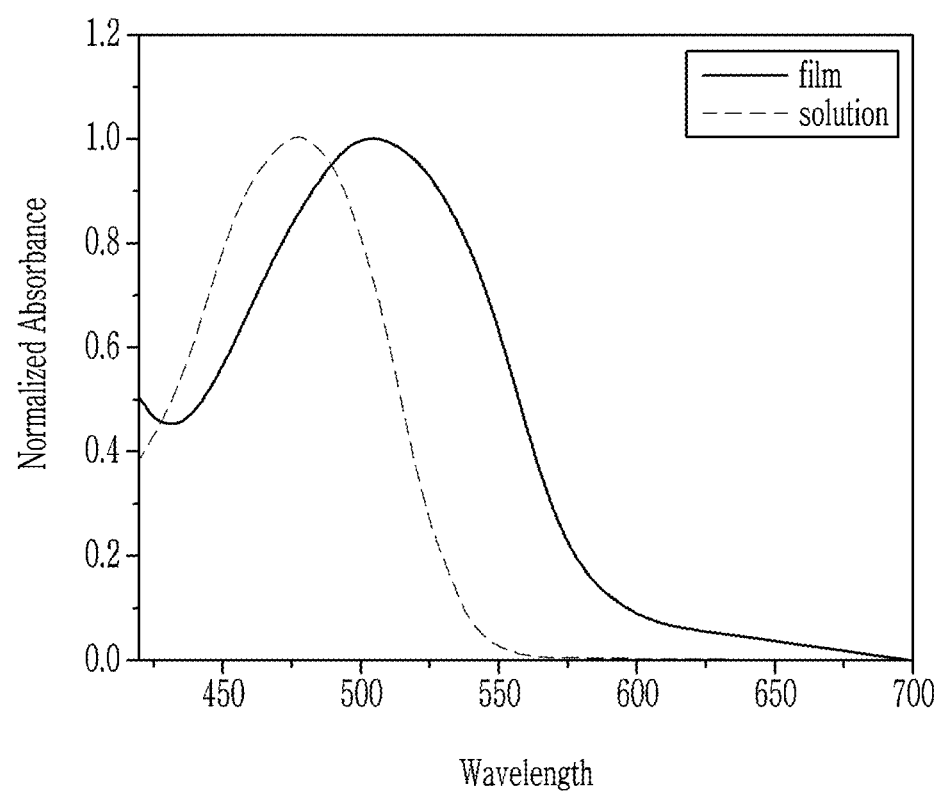
FIG. 6 is a graph showing light-absorption characteristics of the thin film according to Preparation Example 1.
Figure 7:
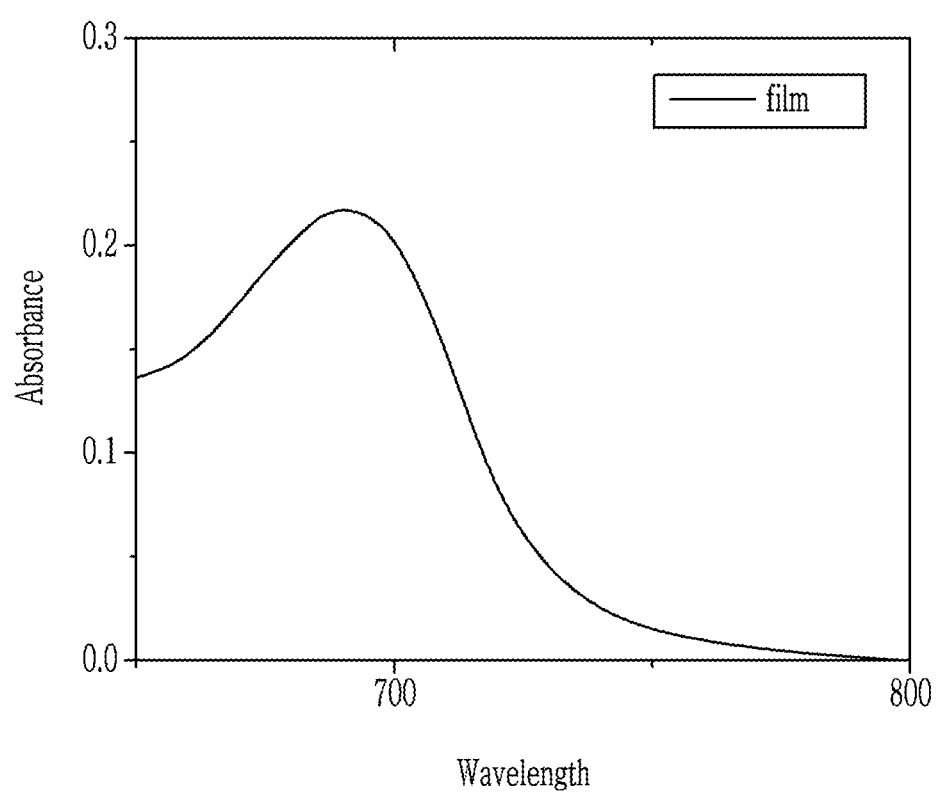
FIG. 7 is a graph showing light-absorption characteristics of the thin film according to Preparation Example 2.

The results are shown in FIGS. 6 and 7 and Table 2.

FIG. 6 is a graph showing light-absorption characteristics of the thin film according to Preparation Example 1, and FIG. 7 is a graph showing light-absorption characteristics of the thin film according to Preparation Example 2

TABLE 2

|  | $\lambda_{max}$ (nm) | Full width at half maximum (FWHM) (nm) |
| --- | --- | --- |
| Preparation Example 1 | 670 | 80 |
| Preparation Example 2 | 510 | 110 |

Referring to FIGS. 6 and 7 and Table 2, it is confirmed that the thin films according to Production Examples 1 and 2 have peak absorption wavelengths in the red wavelength region and the green wavelength region, respectively, and exhibit high wavelength selectivity.

EXAMPLES

Example 1

Preparation of Mixed Solution for Active Layer

A mixed solution for an active layer is prepared by mixing poly(3-hexylthiophene-2,5-diyl) (P3HT) and Compound (8) of Synthesis Example 2 in a weight ratio of 1:1, dissolving the mixture in chloroform at a concentration of 10 mg/ml, and stirring the solution under a nitrogen condition in a globe box at 40° C. all night long.

Manufacture of Organic Device

A glass substrate deposited with patterned ITO is ultrasonic wave-washed with distilled water, acetone, and isopropanol respectively for 20 minutes and then, UV ozone-treated for 20 minutes. Subsequently, on the glass substrate, a conductive thin film is formed to be about 30 nm thick by spin-coating a PEDOT:PSS (Clevios P VP AI4083) conductive polymer solution at 5000 rpm for 30 seconds and baking it at 150° C. for 20 minutes to remove moisture. Subsequently, after moving the substrate having the conductive thin film to a globe box under a nitrogen condition, an active layer is formed on the conductive thin film by spin-coating the mixed solution for an active layer at 1000 rpm for 60 seconds and allowing it to stand at room temperature for 1 hour. Then, on the active layer, an electrode is formed by thermally depositing calcium (Ca) to be 6 nm thick and aluminum (Al) to be 100 nm thick sequentially under high vacuum of less than or equal to $10^{-6}$ torr and heat-treating it on a 70° C. hot plate for 10 minutes finally to manufacture an organic device.

Example 2

A silicon substrate covered with 300 nm-thick $SiO_2$ is ultrasonic wave-washed with deionized water, acetone, and isopropanol sequentially and then, UV ozone-treated for 30 minutes. Subsequently, the surface of the silicon substrate is treated with octadecyltrichlorosilane (OTS) in a gas state and then, moved to a globe box filled with nitrogen, and a 50 nm-thick active layer is formed thereon by thermally depositing Compound (6) of Synthesis Example 1 under high vacuum ($10^{-6}$ to $10^{-5}$ torr) at a speed of 0.1 Å/s to 0.2 Å/s. Subsequently, a source electrode and a drain electrode are formed to be 50 nm thick by thermally depositing gold (Au) through a mask pattern at a speed of 0.3 Å/s to 0.4 Å/s under high vacuum to finally manufacture an organic field-effect transistor (OFET) device.

Evaluation III: Electrical Characteristics

Electrical characteristics of the organic device according to Example 1 are evaluated.

The electrical characteristics of the organic device are evaluated from current density-voltage characteristics (current density-Voltage, J-V), wherein an active region used for the evaluation has an area of 5 mm².

The results are shown in Table 3.

TABLE 3

| VOC [V] | JSC [mA/cm²] | FF | PCE [%] |
|---|---|---|---|
| 0.69 | 1.74 | 0.23 | 0.28 |

Referring to Table 3, the organic device of Example 1 shows satisfactory electrical characteristics.

Evaluation IV: Electrical Characteristics

Electrical characteristics of the organic field-effect transistor according to Example 2 are evaluated.

The electrical characteristics of the organic field-effect transistor device are evaluated from hole and electron mobility in a saturation region of a transfer curve.

The results are shown in Table 4.

TABLE 4

| Hole mobility | $9.2 \times 10^{-4}$ cm²/Vs |
|---|---|
| Electron mobility | $6.1 \times 10^{-2}$ cm²/Vs |

Referring to Table 4, it is confirmed that the organic field-effect transistor according to Example 2 exhibits good charge mobility.

While this disclosure has been described in connection with what is presently considered to be practical example embodiments, it is to be understood that inventive concepts are not limited to the disclosed embodiments, but, on the contrary, is intended to cover various modifications and equivalent arrangements included within the spirit and scope of the appended claims.

What is claimed is:
1. An organic device comprising:
a first electrode and a second electrode facing each other; and
an active layer between the first electrode and the second electrode, the active layer including an n-type semiconductor and a p-type semiconductor capable of providing a pn junction with the n-type semiconductor,
wherein the n-type semiconductor includes a compound represented by Chemical Formula 1:

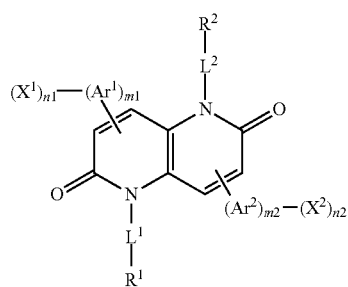

[Chemical Formula 1]

wherein, in Chemical Formula 1,
$L^1$ and $L^2$ are independently a single bond, a substituted or unsubstituted C1 to C20 alkylene group, a substituted or unsubstituted C6 to C30 arylene group, a substituted or unsubstituted divalent C3 to C30 heterocyclic group, a fused ring thereof, or a combination thereof,
$R^1$ and $R^2$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C20 alkoxy group, a substituted or unsubstituted C2 to C20 ester group, a halogen, a cyano group, or a combination thereof, Ar¹ and Ar² are independently a substituted or unsubstituted C6 to C30 arylene group, a substituted or unsubstituted divalent C3 to C30 heterocyclic group, a fused ring thereof, or a combination thereof, X¹ and X² are independently a hydrocarbon cyclic group substituted with an electron withdrawing group, a heterocyclic group substituted with an electron withdrawing group, a substituted or unsubstituted nitrogen-containing cyclic group, a fused ring thereof, or a combination thereof, m1 and m2 are independently an integer ranging from 0 to 3, and n1 and n2 are independently an integer ranging from 0 to 3, provided that n1 and n2 are not simultaneously 0, the p-type semiconductor is a monomer represented by Chemical Formula 2, a HOMO energy level of the p-type semiconductor being about 5.2 eV to about 5.8 eV, EDG-HA-EAG                                [Chemical Formula 2]

In Chemical Formula 2,

HA may be a C2 to C30 heterocyclic group including at least one of S, Se, Te, and Si, EDG may be an electron donating group, and EAG may be an electron accepting group, and a peak absorption wavelength of the compound and a peak absorption wavelength of the p-type semiconductor commonly belong to about 510 nm to about 560 nm.

2. The organic device of claim 1, wherein Ar¹ and Ar² of Chemical Formula 1 are independently a substituted or unsubstituted phenylene group, a substituted or unsubstituted naphthylene group, a substituted or unsubstituted anthracenylene group, a substituted or unsubstituted fluorenylene group, a substituted or unsubstituted thiophenylene group, a substituted or unsubstituted furanylene group, a substituted or unsubstituted selenophenylene group, a substituted or unsubstituted tellurophenylene group, a substituted or unsubstituted silolylene group, a substituted or unsubstituted pyrrolylene group, a substituted or unsubstituted imidazolylene group, a substituted or unsubstituted pyridinylene group, a substituted or unsubstituted pyrimidinylene group, a substituted or unsubstituted triazinylene group, a fused ring thereof, or a combination thereof.

3. The organic device of claim 1, wherein the electron withdrawing group includes a halogen atom, a C1 to C20 haloalkyl group, a cyano group, a dicyanovinyl group, or a combination thereof.

4. The organic device of claim 1, wherein X¹ and X² of Chemical Formula 1 are independently one of groups listed in Group 1:

[Group 1]

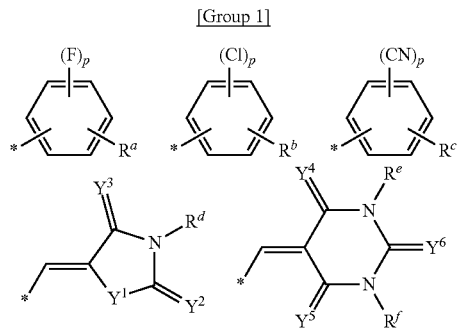

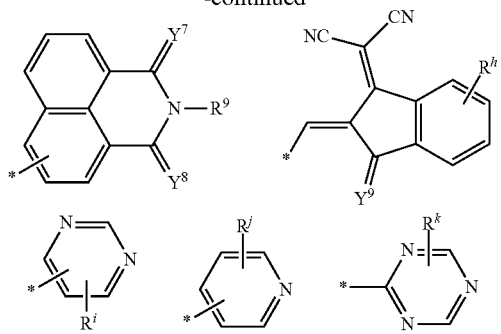

wherein, in Group 1,

Y¹ to Y⁹ are independently O, S, or Se, $R^a$ to $R^k$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof, p is an integer ranging from 1 to 5, and

* is a linking point.

5. The organic device of claim 1, wherein the compound is represented by Chemical Formula 1a:

[Chemical Formula 1a]

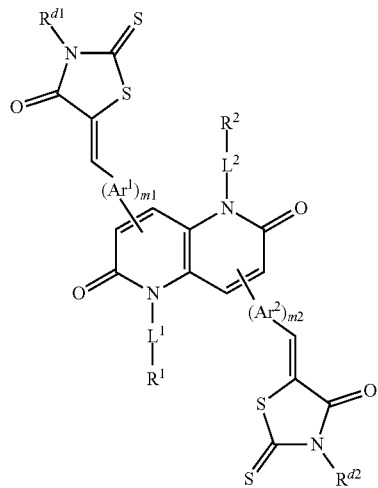

wherein, in Chemical Formula 1a,

L¹ and L² are independently a single bond, a substituted or unsubstituted C1 to C20 alkylene group, a substituted or unsubstituted C6 to C30 arylene group, a substituted or unsubstituted divalent C3 to C30 heterocyclic group, a fused ring thereof, or a combination thereof, R¹ and R² are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C20 alkoxy group, a substituted or unsubstituted C2 to C20 ester group, a halogen, a cyano group, or a combination thereof, Ar¹ and Ar² are independently a substituted or unsubstituted C6 to C30 arylene group, a substituted or unsubstituted divalent C3 to C30 heterocyclic group, a fused ring thereof, or a combination thereof, $R^{d1}$ and $R^{d2}$ are independently hydrogen, a substituted or unsubstituted C1 to C30 alkyl group, a substituted or unsubstituted C6 to C30 aryl group, a substituted or unsubstituted C3 to C30 heterocyclic group, a substituted or unsubstituted C1 to C6 alkoxy group, a substituted or unsubstituted C2 to C20 ester group, a halogen, a cyano group, or a combination thereof, and m1 and m2 are independently an integer ranging from 0 to 3.

6. The organic device of claim 5, wherein $Ar^1$ and $Ar^2$ of Chemical Formula 1a are independently a substituted or unsubstituted phenylene group, a substituted or unsubstituted naphthylene group, a substituted or unsubstituted anthracenylene group, a substituted or unsubstituted fluorenylene group, a substituted or unsubstituted thiophenylene group, a substituted or unsubstituted furanylene group, a substituted or unsubstituted selenophenylene group, a substituted or unsubstituted tellurophenylene group, a substituted or unsubstituted silolylene group, a substituted or unsubstituted pyrrolylene group, a substituted or unsubstituted imidazolylene group, a substituted or unsubstituted pyridinylene group, a substituted or unsubstituted pyrimidinylene group, a substituted or unsubstituted triazinylene group, a fused ring thereof, or a combination thereof.

7. The organic device of claim 1, wherein a HOMO energy level of the compound is about 5.2 eV to about 5.8 eV.

8. The organic device of claim 1, wherein the active layer further includes fullerene or a fullerene derivative.

9. An electronic device comprising:
the organic device of claim 1.

10. An image sensor comprising:
the organic device of claim 1.

11. The image sensor of claim 10, further comprising:
a semiconductor substrate on the organic device, and
wherein the semiconductor substrate includes a plurality of photodiodes.

12. The image sensor of claim 11, wherein
the organic device is configured to selectively absorb a first visible light in one of a red wavelength region, a green wavelength region, and a blue wavelength region,
the photodiode includes a first photodiode and a second photodiode,
the first photodiode is configured to sense second visible light in a red wavelength region, a green wavelength region, or a blue wavelength region, and
the second photodiode is configured to sense third visible light in a red wavelength region, a green wavelength region, or a blue wavelength region, and
the first visible light, the second visible light, and the third visible light are different from each other.

13. The image sensor of claim 12, further comprising:
a color filter layer on or under the organic device.

14. The image sensor of claim 13, wherein
the color filter layer includes a first color filter and a second color filter,
the first color filter overlaps the first photodiode and is configured to selectively transmit light including the second visible light, and
the second color filter overlaps the second photodiode and is configured to selectively transmit light including the third visible light.

15. An electronic device comprising:
the image sensor of claim 10.

* * * * *